United States Patent
Brown et al.

(10) Patent No.: US 10,464,063 B2
(45) Date of Patent: Nov. 5, 2019

(54) MICROFLUIDICS CHIP WITH SENSOR DIE CLAMPING STRUCTURES

(71) Applicant: e-SENS, Inc., Salt Lake City, UT (US)

(72) Inventors: Richard B. Brown, Salt Lake City, UT (US); Ondrej Novak, North Salt Lake, UT (US)

(73) Assignee: e-SENS, Inc., Salt Lake City, UT (US)

( * ) Notice: Subject to any disclaimer, the term of this patent is extended or adjusted under 35 U.S.C. 154(b) by 357 days.

(21) Appl. No.: 15/482,277

(22) Filed: Apr. 7, 2017

(65) Prior Publication Data

US 2018/0290137 A1 Oct. 11, 2018

(51) Int. Cl.
*B01L 3/00* (2006.01)
*G01N 27/333* (2006.01)

(52) U.S. Cl.
CPC ....... *B01L 3/502715* (2013.01); *B01L 3/5027* (2013.01); *B01L 3/502707* (2013.01); *G01N 27/333* (2013.01); *B01L 2200/12* (2013.01); *B01L 2300/0627* (2013.01); *B01L 2300/0645* (2013.01); *B01L 2300/0663* (2013.01); *B01L 2300/0887* (2013.01)

(58) Field of Classification Search
CPC ............. B01L 3/502715; B01L 3/5027; B01L 3/502707; B01L 2300/0663; B01L 2300/0645; B01L 2300/0627; B01L 2300/0887; B01L 2200/12; G01N 27/333
See application file for complete search history.

(56) References Cited

U.S. PATENT DOCUMENTS

| 5,700,360 | A  | 12/1997 | Chan et al. |
| 6,764,652 | B2 | 7/2004  | Hower et al. |
| 7,258,837 | B2 | 8/2007  | Yager et al. |

(Continued)

FOREIGN PATENT DOCUMENTS

| EP | 1353751 | 4/2011 |
| KR | 20030014527 A | 2/2003 |

(Continued)

OTHER PUBLICATIONS

Lin et al "Integrating solid-state sensor and microfluidic devices for glucose, urea and creatinine detection based on enzyme-carrying alginate microbeads" Biosensors and Bioelectronics 43 (2013) 328-335 (Year: 2013).*

(Continued)

*Primary Examiner* — Dennis White
(74) *Attorney, Agent, or Firm* — Alliance IP, LLC

(57) ABSTRACT

Aspects of the embodiments are directed to a microfluidic chip that includes a plurality of openings to expose a microfluidic channel. The plurality of openings are within a recessed area of the microfluidics chip, the recess defining a surface onto which a sensor die can be clamped. The surface can include a clamping bump that contacts a membrane of a solid-state chemical sensor. The surface can also include a glue stop that, in some embodiments, can act as a spacer to prevent over-compression of the sensor die as it is clamped onto the microfluidic chip. The microfluidic chip can include a rigid structure, such as a printed circuit board, that is affixed to a top surface of the microfluidic chip. The rigid structure can include contact pads that are electrically connected to sensor electrodes on the sensor die by a wire.

20 Claims, 20 Drawing Sheets

(56) References Cited

U.S. PATENT DOCUMENTS

| | | |
|---|---|---|
| 7,438,851 B2 | 10/2008 | Hower et al. |
| 7,988,838 B2 | 8/2011 | Dipiazza et al. |
| 9,017,611 B2 | 4/2015 | Lin et al. |
| 2008/0308418 A1 | 12/2008 | Dipiazza et al. |

FOREIGN PATENT DOCUMENTS

| | | |
|---|---|---|
| WO | 2002058846 A2 | 8/2002 |
| WO | WO 2002/058846 | 8/2002 |

OTHER PUBLICATIONS

Lin, Yen-Heng et al., "Integrating Solid-State Sensor and Microfluidic Devices for Glucose, Urea and Creatinine Detection Based on Enzyme-Carrying Alginate Microbeads," Biosensors and Bioelectronics, 2013 vol. 43, pp. 328-335.

PCT International Search Report and Written Opinion in PCT International Application Serial No. PCT/US2018/026428 dated Aug. 20, 2018 (7 pages).

Franklin, Robert K. et al., "2.12 Chemical Sensors", The University of Michigan Ann Arbor, MI, Sensicore, Inc., Ann Arbor, MI, The University of Utah, Salt Lake City, UT, Elsevier B.V., 2008 (pp. 432-461) (29 pages).

\* cited by examiner

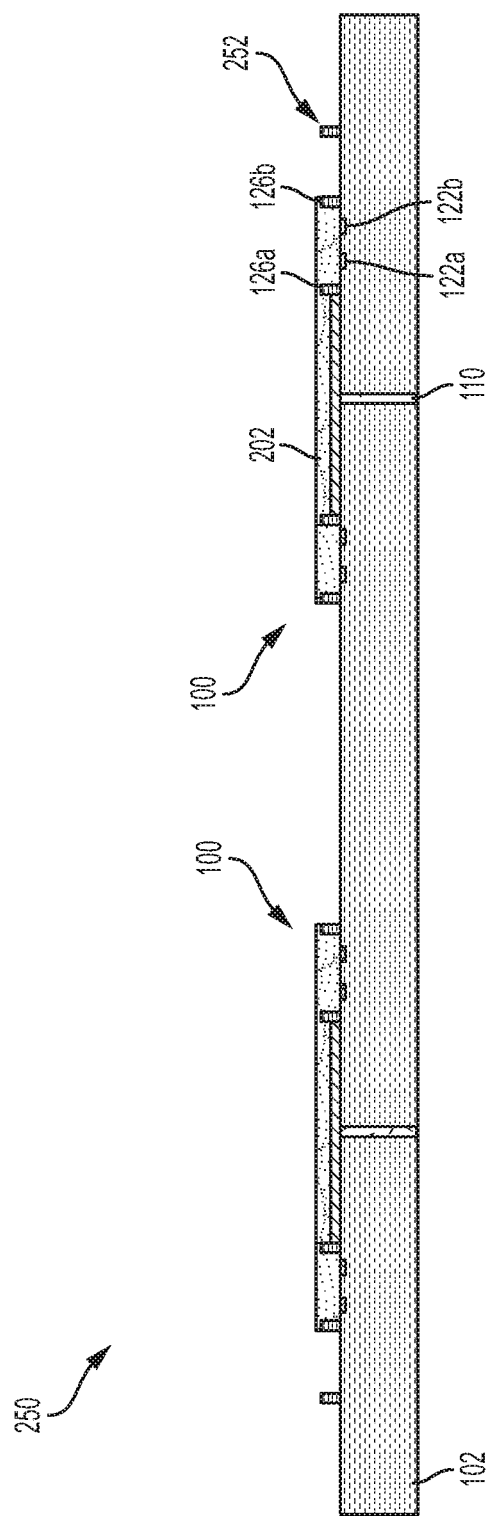

A-A

B-B

B-B(ALT)

B-B(ALT)

B-B (ALT)

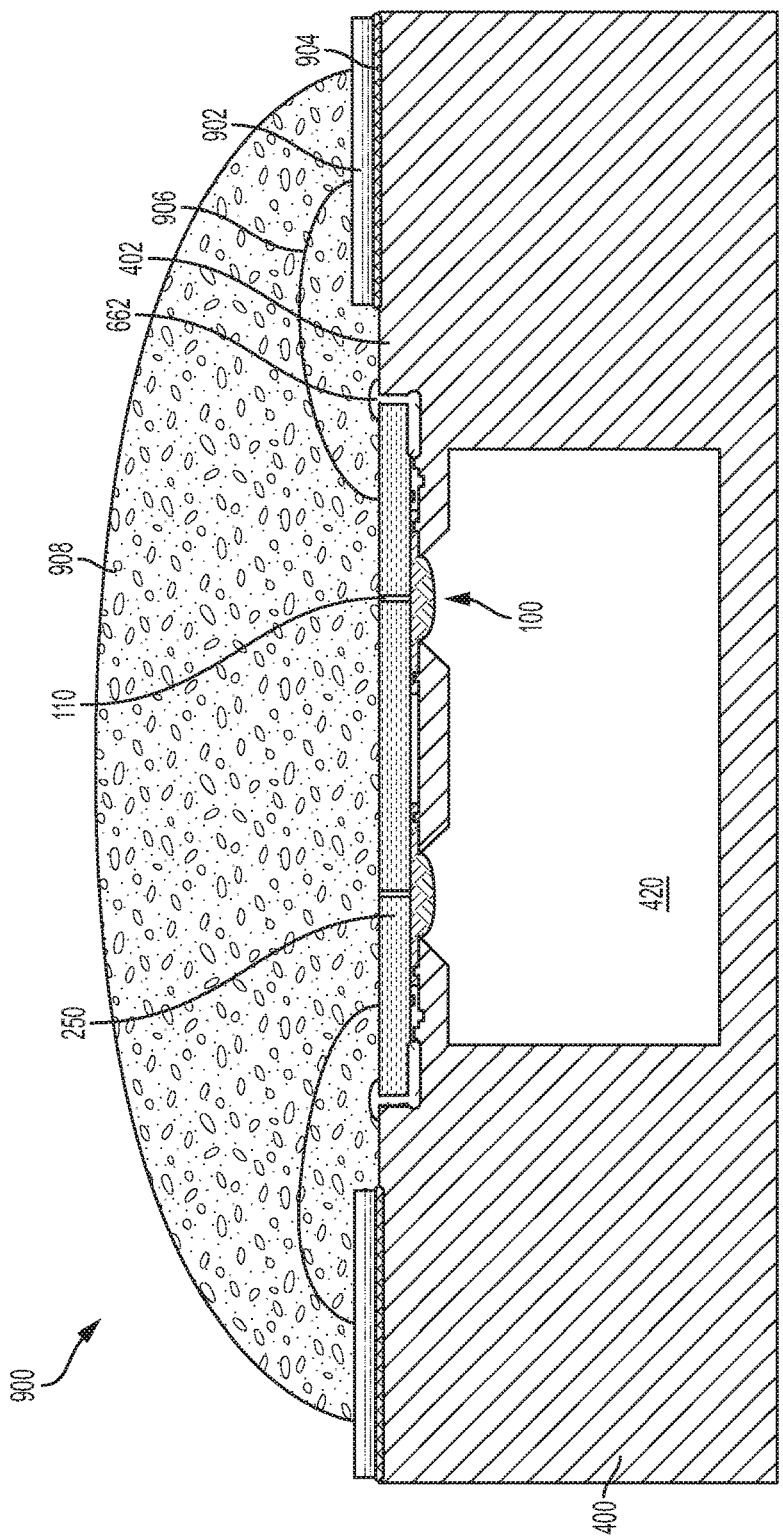

MICROFLUIDICS CHIP WITH SENSOR DIE CLAMPING STRUCTURES

TECHNICAL FIELD

This disclosure pertains to microfluidics chips with sensor die clamping structures, and more particularly, to sensor die clamping structures for sensor dies having backside wire bonding.

BACKGROUND

Chemical sensors can be fabricated using semiconductor technology. The use of semiconductor manufacturing can result in a reduction of size of the chemical sensor as well as mass fabrication of chemical sensors, thereby reducing per unit cost of each sensor. More generally, the use of semiconductor manufacturing to manufacture sensors produces the same or similar benefits as it does for electrical circuits: low cost per sensor, small size, and highly reproducible behavior.

Semiconductor manufacturing technology also provides precise control of layer thickness and lateral dimensions, so that the sensors can be miniaturized, and so that they will have well-controlled characteristics. By making the sensors small, one can calibrate them with small volumes of calibration solution. Sample volumes can be small (which may not be important in testing water, but may be important in testing other solutions, such as blood samples from newborns). Operation of the sensors also requires rinsing between samples, and storage in a controlled solution. Volumes of all of these solutions can be smaller if the sensors are miniaturized, as they are on the silicon substrates.

SUMMARY

Chemical sensors, such as ion selective electrodes (ISEs), can be used in microfluidic sensor chips. The polymeric sensing membranes used to form the ISEs do not adhere well to silicon nitride or silicon dioxide surfaces that are often used to insulate silicon dies and to protect the conducting layers in the die from the solution under test and from the internal filling solution that is between the electrode and the membrane. Poor membrane-to-sensor-die adhesion results in unreliable sensors and short sensor lifetimes. Polymeric membranes can be adhered to the sensor surface by salinizing the silicon dioxide surface and interposing adhesion layers between this surface and the polymeric membrane. The deposition of these additional layers adds complexity to the manufacturing process, and the components of the adhesion layers can poison the sensing membrane. This disclosure describes a mechanical method of adhering a polymeric membrane to the surface of a solid-state liquid chemical sensor, thereby making the sensor more reliable and robust, and giving the sensor a longer lifetime.

Aspects of the embodiments are directed to a microfluidic chip that includes a top surface and an intermediate surface. The intermediate surface defining a microfluidic channel can include a microfluidics channel in the microfluidic chip; an opening in the intermediate surface exposing a microfluidic channel; a first surface surrounding the opening; and a solid-state chemical sensor residing on a sensor die, at least a portion of the solid-state chemical sensor in contact with the first surface of the microfluidic chip, the solid-state chemical sensor exposed to the microfluidics channel.

In some embodiments, the solid-state chemical sensor includes a sensor substrate residing on the microfluidic chip, the sensor substrate comprising a sensor device residing on a sensor-side of the substrate. The sensor-side of the sensor device can face the microfluidics channel. The sensor device can include a sensor-side electrode on the sensor-side of the substrate, the sensor-side electrode facing the microfluidics channel; a first polymer ring surrounding the sensor-side electrode; a second polymer ring surrounding the first polymer ring; a polymeric membrane encapsulating the sensor-side electrode and being contained by a second polymer ring.

In some embodiments, the first surface is in contact with the polymeric membrane at a location between the first polymer ring and the second polymer ring, the first surface clamping the sensor die to the microfluidic chip.

Some embodiments can also include a second raised surface surrounding the first raised surface; and the substrate of the sensor device being in contact the second raised surface.

In some embodiments, the second raised surface defines an open space between the top surface and the intermediate surface, the microfluidic chip further comprising an adhesive substance in the space, the adhesive substance contacting the substrate, and securing the substrate to the intermediate surface.

In some embodiments, the sensor die comprises a plurality solid-state chemical sensors, each of the plurality of solid-state chemical sensors exposed to the microfluidics channel.

In some embodiments, the first surface is a first raised surface, the microfluidic chip further comprises a second raised surface adjacent the first raised surface.

In some embodiments, the first raised surface is lower in height than the second raised surface.

In some embodiments, the second raised surface contacts the sensor die.

Some embodiments also include a trench between the first raised surface and the second raised surface.

In some embodiments, the sensor die is clamped to the microfluidic chip by an adhesive.

In some embodiments, the sensor die can include a sensor side and a backside. The backside can including a backside electrode; and the sensor die can include a through-silicon via electrically connecting the sensor-side and the backside electrode.

Some embodiments also include a rigid structure affixed to the microfluidic chip, the printed circuit board comprising a contact pad, the backside electrode electrically connected to the contact pad by a wire.

In some embodiments, the rigid structure comprises a printed circuit board.

In some embodiments, the rigid structure is affixed to the microfluidic chip by one or more screws.

In some embodiments, the rigid structure is affixed to the microfluidic chip by doubled sided tape.

In some embodiments, the sensor die comprises a plurality of sensor devices.

In some embodiments, the opening is defined by a conical shape exposing the microfluidics channel.

Aspects of the embodiments are directed to a method for forming a microfluidic system comprising a sensor device. The method can include providing a microfluidic chip, the microfluidic chip comprising a sensor device mounting surface, the sensor device mounting surface comprising an opening revealing a microfluidic channel and a first raised surface surrounding the opening and a second raised surface surrounding the first raised surface; providing a substrate with a chemical sensor device onto the sensor device mounting surface, the chemical sensor device comprising an ion-selective sensor facing the microfluidic channel, the chemical sensor device further comprising a polymeric membrane facing the microfluidic channel, the substrate contacting the second raised surface and the first raised surface contacting the membrane between two polymeric rings residing on the sensor die; applying a compressive load to the substrate in a direction towards the sensor device mounting surface; applying an adhesive substance to the substrate and an outer sidewall of the second raised surface; and curing the adhesive substance under the compressive load.

In some embodiments, the chemical sensor comprises an electrode on a backside of the chemical sensor device electrically connected to the ion selective sensor and opposite the microfluidic channel. The method can also include adhering a printed circuit board to the microfluidic chip, the printed circuit board comprising an electrical contact pad; and electrically connecting the electrode on the backside of the chemical sensor to the electrical contact pad on the printed circuit board.

BRIEF DESCRIPTION OF THE DRAWINGS

FIG. 2B is a schematic diagram of a sensor die that includes multiple sensor devices in accordance with embodiments of the present disclosure.

FIG. 9A is a schematic diagram of a side sectional view of a sensor die clamped to a microfluidic chip and electrically coupled to a printed circuit board in accordance with embodiments of the present disclosure.

Figure 1:
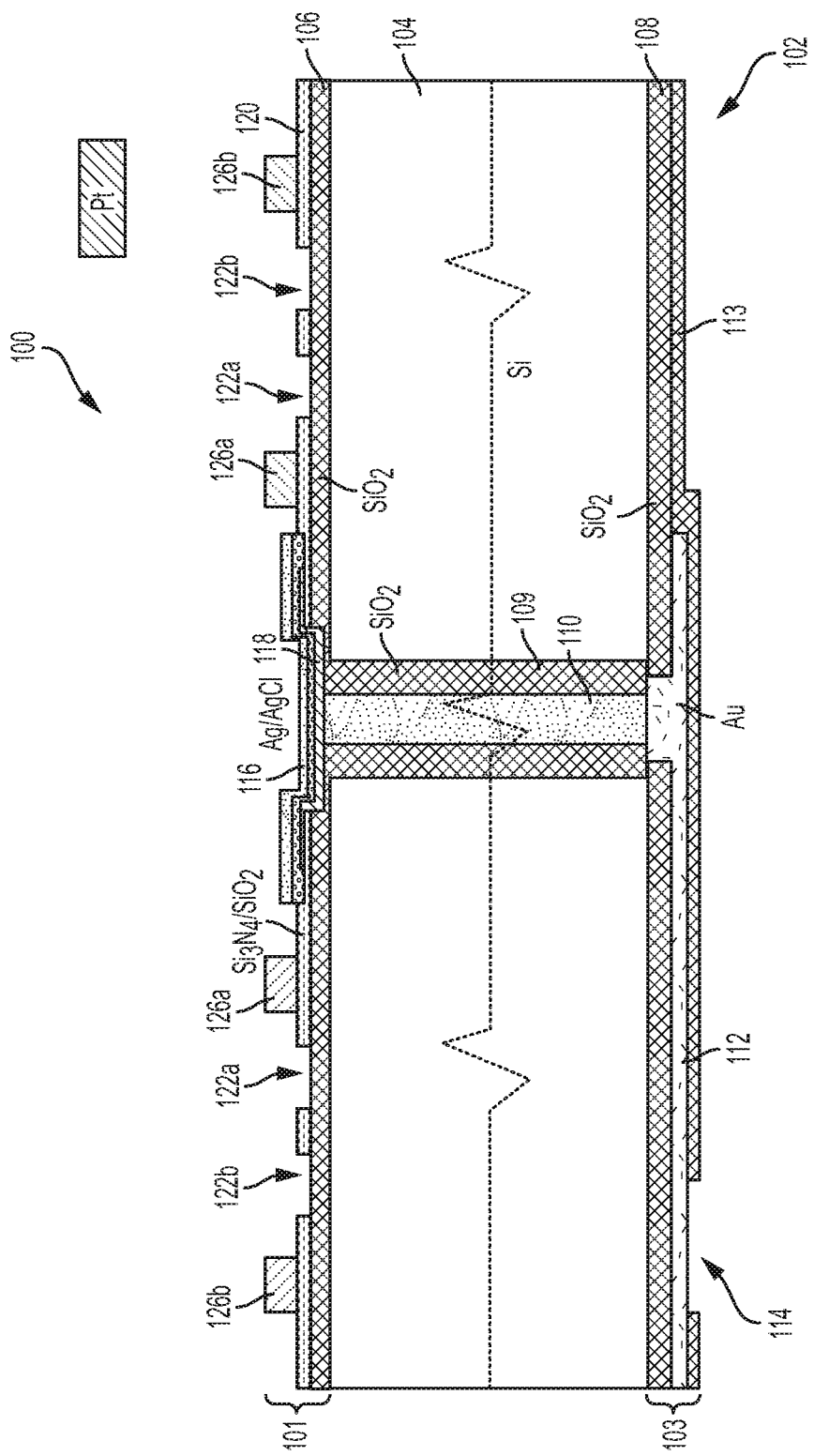
FIG. 1 is a schematic diagram of a sensor device in accordance with embodiments of the present disclosure.

Figures are not drawn to scale.

DETAILED DESCRIPTION

Chemical sensors, such as ion selective electrodes (ISEs) can be made using ionophore-doped polymeric membranes. For example, an ISE can use an ion-selective polymeric membrane that contains the ionophore Valinomycin for detecting potassium, or 4-tert-Butylcalix[4]arene-tetraacetic acid tetraethyl ester for detecting sodium. The ionophore is a selective binding site for the analyte. The polymeric membrane establishes a barrier between the sensor electrode and an analyte solution. The polymeric membrane facilitates the introduction of an analyte to the ionophore, which binds the charged ion, creating a charge separation between the interior of the polymeric membrane and the external aqueous solution. The charge separation creates a voltage that can be measured to determine the presence and concentration of the specific analyte. An example chemical sensor is described in U.S. patent application Ser. No. 15/204,371 filed on Jul. 7, 2016, the entire contents of which are incorporated by reference herein.

Polymeric membranes do not adhere well to silicon nitride surfaces that are often used to insulate the silicon and to protect the silicon and other conducting layers from the solutions under test and from the internal filling solution that is between the electrode and the membrane. Additionally, polymeric membranes adhere better to silicon dioxide than to silicon nitride.

In this disclosure, a "gripping trench" is formed in the silicon nitride, with the bottom of the trench being the silicon dioxide passivation layer. The trench surrounds the entirety of the silver/silver chloride electrode. The polymeric sensing membrane can be deposited on the electrode (or on the hydrogel buffer solution) and the gripping trench to form a seamless membrane filling the gripping trench around the entire electrode. Electrical contact to the silver/silver chloride electrode is made with a conductive via (e.g., a through-silicon via) through the silicon substrate, from sensor-side to backside.

The backside electrode electrically coupled to the silver/silver chloride electrode through a via eliminates the need to wire-bond to the front side of the wafer, making practical the use of a physical clamp over the outer portion of the sensing membrane to hold the membrane onto the sensor die. The trench (also referred to herein as a gripping trench) is filled with cured membrane material, giving the clamp the ability to hold the outer portion of the membrane firmly in place, even when the center of the membrane stretches due to osmotic pressure in the internal filling solution. The gripping trenches can completely encircle the active sensor, thereby eliminating areas in which solution shunts could form between the internal fill and the sample solution. Polyimide, SU-8, or other high-aspect-ratio photopolymers can be used to form structures (e.g., polyimide rings or SU-8 rings) to "contain" the deposited internal fill solution and membrane cocktail (e.g., through surface tension). In this disclosure, the specific embodiment that uses polyimide rings is described, for easy of discussion. It should be noted, however, that other polymers can be used for the polymer rings without deviating from the scope of the disclosure.

FIG. 1 is a schematic diagram of a sensor device 100 in accordance with embodiments of the present disclosure. The schematic diagram shown in FIG. 1 is not drawn to scale. Sensor device 100 includes a substrate 102. Substrate 102 can include silicon 104, such as silicon <100>. The substrate 102 includes a "sensor-side" 101 and a "backside" 103. The sensor-side 101 can include a sensor-side first passivation layer 106, which can be a silicon dioxide ($SiO_2$) layer 106. The substrate backside 103 can also include a backside passivation layer 108, which can be silicon dioxide 108. The term "layer" is used throughout this disclosure and is meant to include one or more layers of a material, and is not limited to meaning a monolayer or single atomic layer of a material.

The silicon substrate 102 can be doped to make it conductive, and can include an electrically isolated doped region 110. The electrically isolated doped region 110 can include a p-type dopant, such as a boron p-type dopant. The sensor device 100 includes sensor-side electrode 116 and a backside electrode 112. The electrically isolated doped region 110 can electrically connect the sensor-side electrode 116 with the backside electrode 112 and can be electrically isolated from the rest of the substrate by a passivation layer (e.g., SiO2 layer 109). This electrically isolated doped region 110 can be referred to as a via 110 (which can be a through-silicon via 110).

The backside electrode 112 can include a conductive material, such as a metal. In some embodiments, the backside electrode 112 may include gold (Au). The backside electrode 112 can be accessed by a bonding pad 114. In some embodiments, another backside passivation layer 113 can be deposited over the backside electrode to protect the backside 103 from damage. The backside passivation layer 113 can include silicon nitride or silicon dioxide.

The sensor-side 101 can include a sensor-side electrode 116. The via 110 is physically and electrically connected to the sensor-side electrode 116. The sensor-side electrode can include silver (Ag) and silver chloride (AgCl). Silver chloride has a stable interfacial potential to the internal filling solution and desirable Ohmic properties.

In some embodiments, the via 110 is electrically and physically connected to a thin platinum disc 118. The platinum disc 118 can be completely covered by silver. The silver has a chloridized surface, resulting in a silver/silver-chloride electrode.

On the sensor-side first passivation layer 106, is a sensor-side second passivation layer 120. The sensor-side second passivation layer 120 can include silicon nitride ($Si_3N_4$) and silicon dioxide ($SiO_2$). As an example, the sensor-side second passivation layer 120 can be silicon nitride, or can include a layer of silicon dioxide on top of silicon nitride.

In some embodiments, adjacent to the sensor-side electrode 116 is a polyimide ring structure 126a residing on the sensor-side second passivation layer 120. The polyimide ring 126a can be circular or substantially circular, and surround the sensor-side electrode 116.

A gripping trench 122a can be etched into the sensor-side second passivation layer 120 adjacent to the polyimide ring structure 126a. The gripping trench 122a can be a first gripping trench 122a; multiple gripping trenches, such as the second gripping trench 122b can be formed adjacent to the first gripping trench 122a. The first and second gripping trenches 122a and 122b can be circular or substantially circular and can surround the sensor-side electrode 116 (and in some embodiments, surround the polyimide ring 126a).

The gripping trenches 122a and 122b can be etched to stop on the underlying sensor-side first passivation layer 106 (i.e., the silicon dioxide 106). The shape of the gripping trenches 122a and 122b prevent the membrane from pulling toward the center of the sensor when the membrane hydrates, creating osmotic pressure in the internal filling solution.

In some embodiments, a second polyimide ring 126b can reside on the sensor-side second passivation layer 120. The second polyimide ring 126b can be circular or substantially circular and can surround the sensor-side electrode 116 and the gripping trench 122a (and 122b or others, if present).

Though described as a silicon substrate, substrate 102 could in some embodiments be composed of glass or ceramic or other suitable material.

Figure 2A:
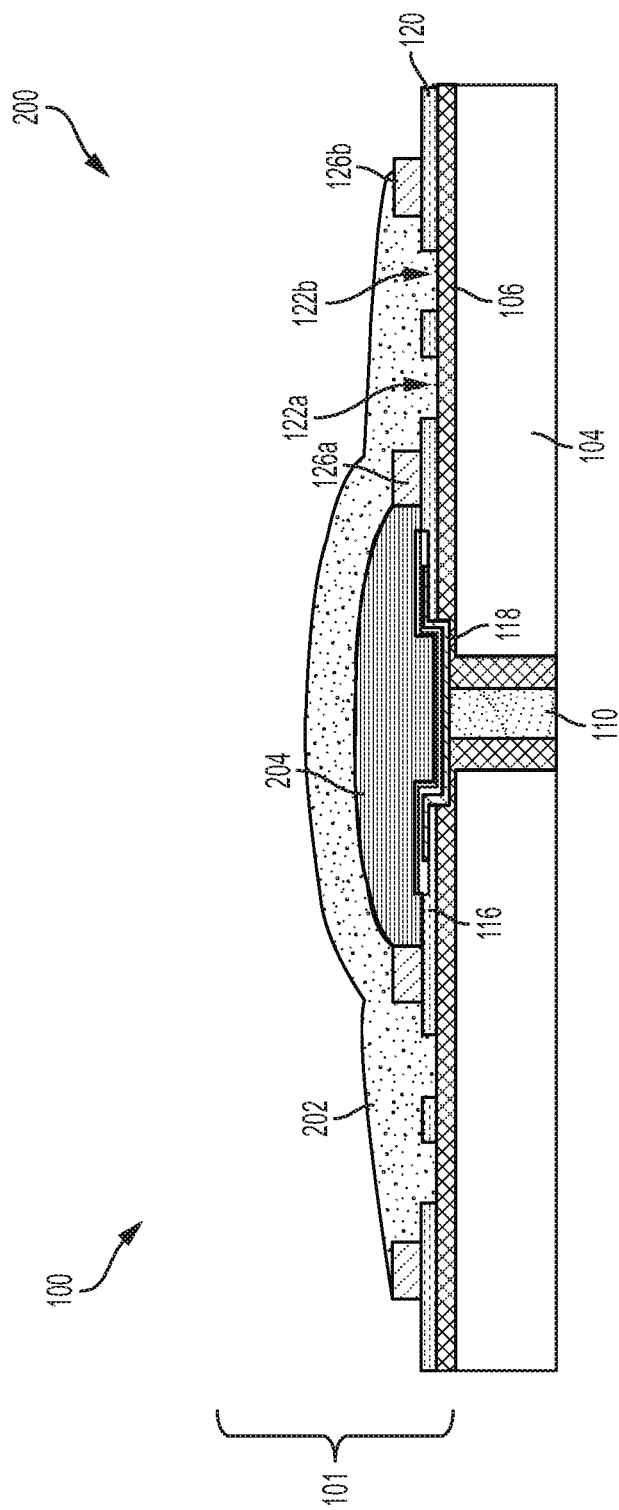
FIG. 2A is a schematic diagram of a sensor device that includes a polymeric membrane in accordance with embodiments of the present disclosure.

FIG. 2A is a schematic diagram 200 of a sensor device 100 that includes a polymeric membrane 202 in accordance with embodiments of the present disclosure. The diagram 200 of FIG. 2 shows the sensor device 100 of FIG. 1 with the addition of the polymeric membrane 202 as well as the hydrogel buffer solution 204. In FIG. 2, the first polyimide ring 126a can be shown to define the size of the hydrogel buffer solution 204. The outer polyimide ring 126b defines the size of the polymeric membrane 202 that acts as the transducer of the sensor device 100.

Also shown in FIG. 2A is the polymeric membrane 202 filling gripping trenches 122a and 122b. The polymeric membrane 202 can be "confined" by the second polyimide ring 126b based on the shape of the polyimide ring and based on surface tension of the deposited polymeric membrane cocktail solution, composed of the membrane components and organic solvent.

The polymeric membrane 202 is shown to contact the hydrogel buffer solution 204. The hydrogel buffer solution 204 can reside within the first polyimide ring 126a and contact the electrode 116. To provide a well-poised electrical contact to the polymeric membrane 202, a hydrogel buffer solution 204 can be used between the silver/silver chloride electrode 116 and the polymeric membrane 202. This hydrogel-based filling solution 204 is buffered with high concentrations of salts. The polymeric membrane 202 hydrates when exposed to aqueous solutions, and the high salt content of the hydrogel buffer solution 204 can generate considerable osmotic pressure on the polymeric membrane 202 as water moves through the membrane into the hydrogel.

By avoiding the need to put bonding wires on the sensor side of the die, the via 110 allows a mechanical clamp to be used to hold the polymeric membrane tightly onto the sensor device. The mechanical clamp and the gripping trench(es) 122a (and 122b) prevent the osmotic pressure created by the hydrogel buffer solution 204 from causing the hydrogel buffer solution to leak out from under the polymeric membrane 202, forming an electrical short circuit path around the membrane.

FIG. 2B is a schematic diagram of a sensor die 250 that includes multiple sensor devices in accordance with embodiments of the present disclosure. Sensor die 250 can include a substrate 102, as described above. The substrate 102 can include multiple sensors 100. Each sensor 100 can include a membrane 202 confined by rings 126a and 126b. The membrane can cover gripping trenches 122a and 122b. A through-silicon via 110 can electrical connect the sensor 100 with a metal electrode on the substrate 102. The substrate 102 can also include a ring 252. Ring 252 can be formed to be the same or similar height as the rings 126a and 126b. Ring 252 can be a polyimide ring formed in the same or similar way as rings 126a and 126b. Ring 252 can be used as a glue stop, as described below. The sensor die 250 can include a plurality of sensors 100, and two are shown in FIG. 2B as an example.

Figure 3:
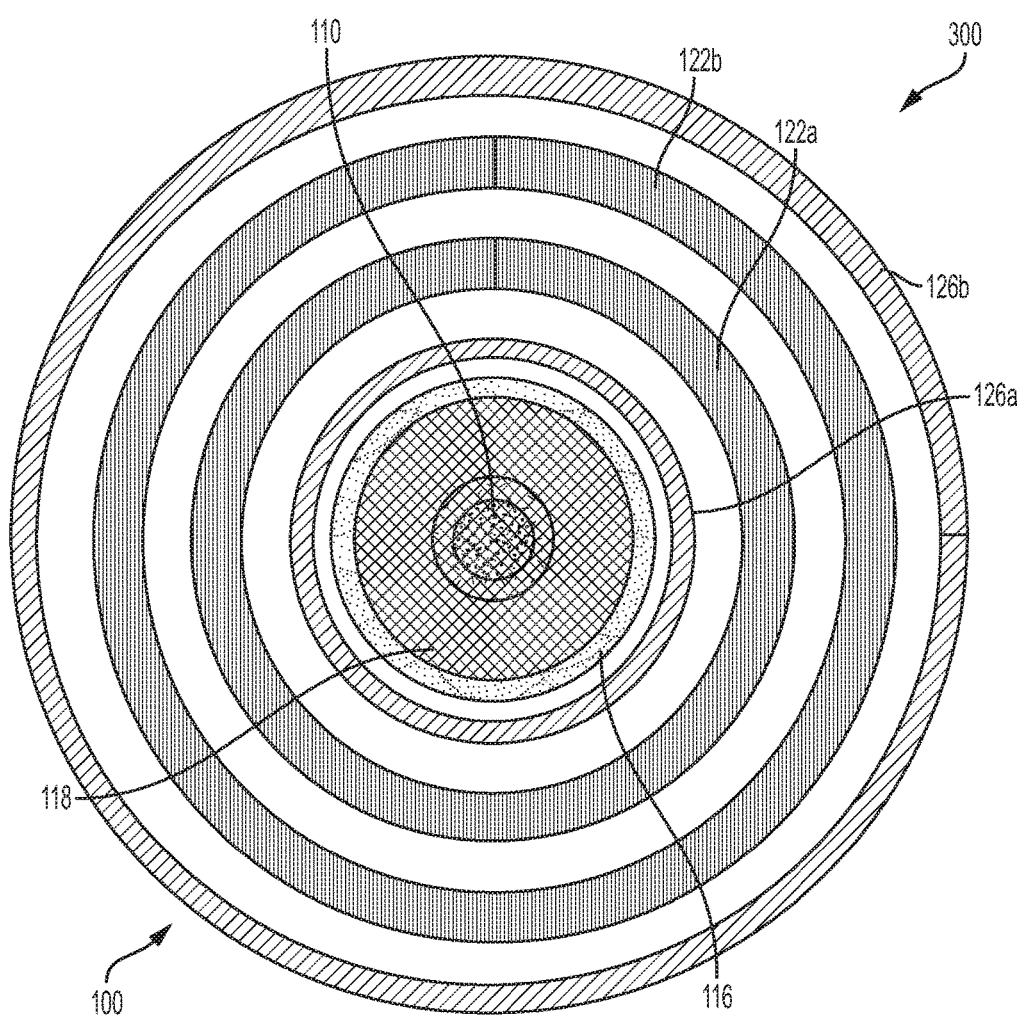
FIG. 3 is a schematic diagram of a top-down view of a sensor device in accordance with embodiments of the present disclosure.

FIG. 3 is a schematic diagram 300 of a top-down sectional illustration of a sensor device 100 in accordance with embodiments of the present disclosure. At the center is the via 110. Above the via 110 is the platinum disk 118. Above the platinum disk 118 is the silver/silver chloride electrode 116. Around the electrode 116 is the first polyimide ring 126a. Gripping trenches 122a and 122b surround the first polyimide ring 126a. The second polyimide ring 126b surrounds the gripping trenches 122a and 122b.

Figure 4:
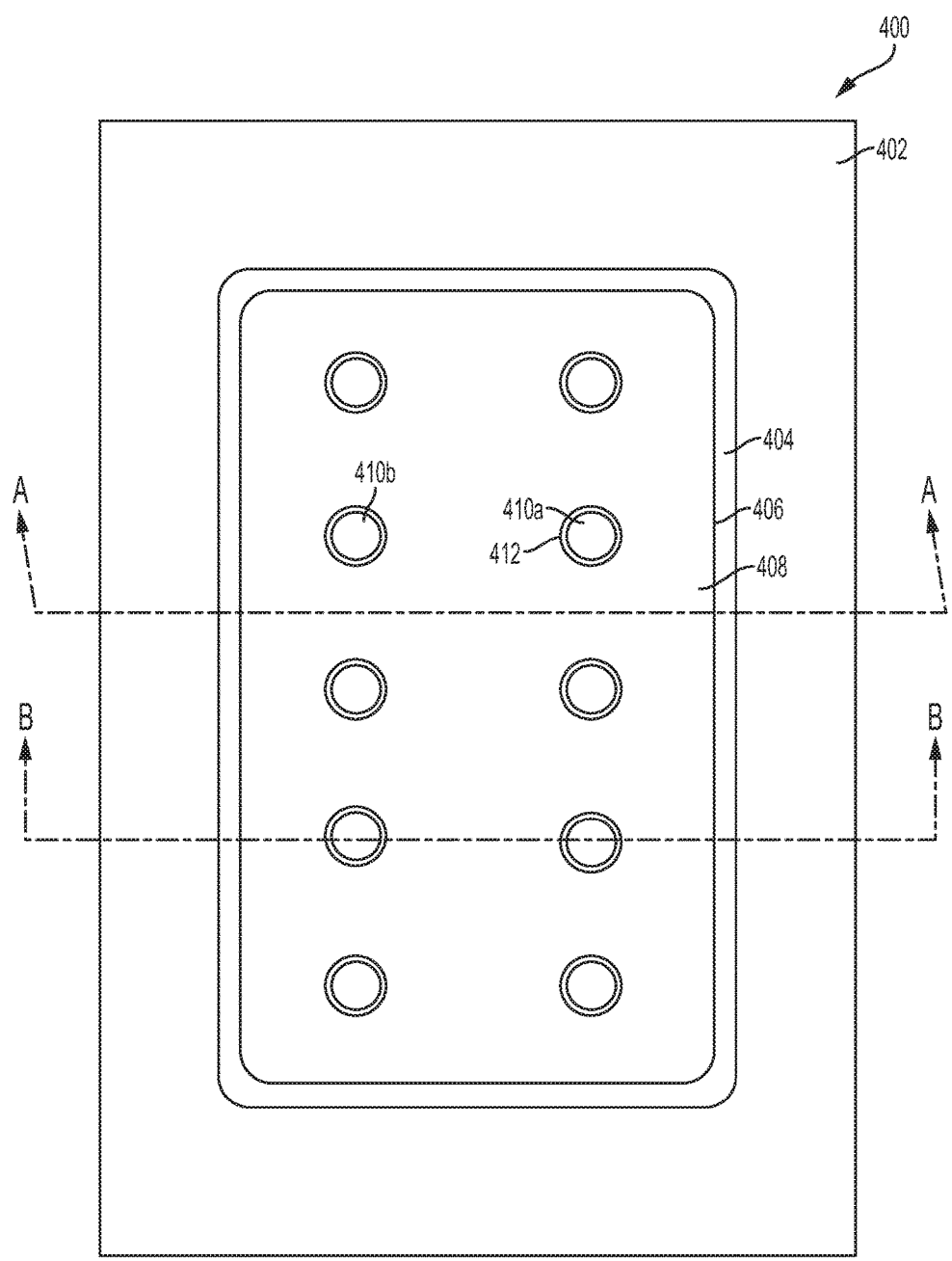
FIG. 4 is a schematic diagram of a top-down view of a portion of a microfluidic chip that includes multiple fluid channel access areas in accordance with embodiments of the present disclosure.

FIG. 4 is a schematic diagram of a top-down view of a portion of a microfluidic chip that includes multiple fluid channel access areas in accordance with embodiments of the present disclosure. The microfluidic chip 400 includes a top surface 402, a first intermediate surface 404, and a second intermediate surface 408. The first intermediate surface 404 is lower in height than the top surface 402, defining a step-wise transition from the first intermediate surface 404 to the top surface 402. The second intermediate surface 408 is lower in height than the first intermediate surface 404. The second intermediate surface 408 can include a glue stop 406. Glue stop 406 can be a raised portion extending from the second intermediate surface 408. Glue stop 406 can be substantially rectangular in shape. The glue stop 406 can have a height, such as 20 microns or similar.

The second intermediate surface 408 can include one or more sensor locations 410. Each sensor location 410 can include an opening to receive a chemical sensor device, such as sensor device 100. The second intermediate surface 408 can include a clamp bump 412 proximate to and surrounding the opening. The clamp bump 412 can have a width of about 100 microns and a height of about 10-15 microns. In some embodiments, the glue stop 406 can be taller than the clamping bump. In some embodiments, the glue stop 406 and the clamping bump 410 can have substantially the same or similar height dimensions.

The microfluidic chip 400 can have an x-dimension of (or substantially of) 3660 mm and a y-dimension of (or substantially of) 6820 mm. Ten chemical sensor locations are shown, which can be located at various locations on microfluidic chip 400. Any combination of chemical sensor locations can be used (e.g., a single sensor can be used or a plurality in any combination of locations can be used).

The microfluidic chip 400 can be made of a poly methyl methacrylate (PMMA), polycarbonate, polystyrene, or other thermoplastic polymer.

Figure 5:
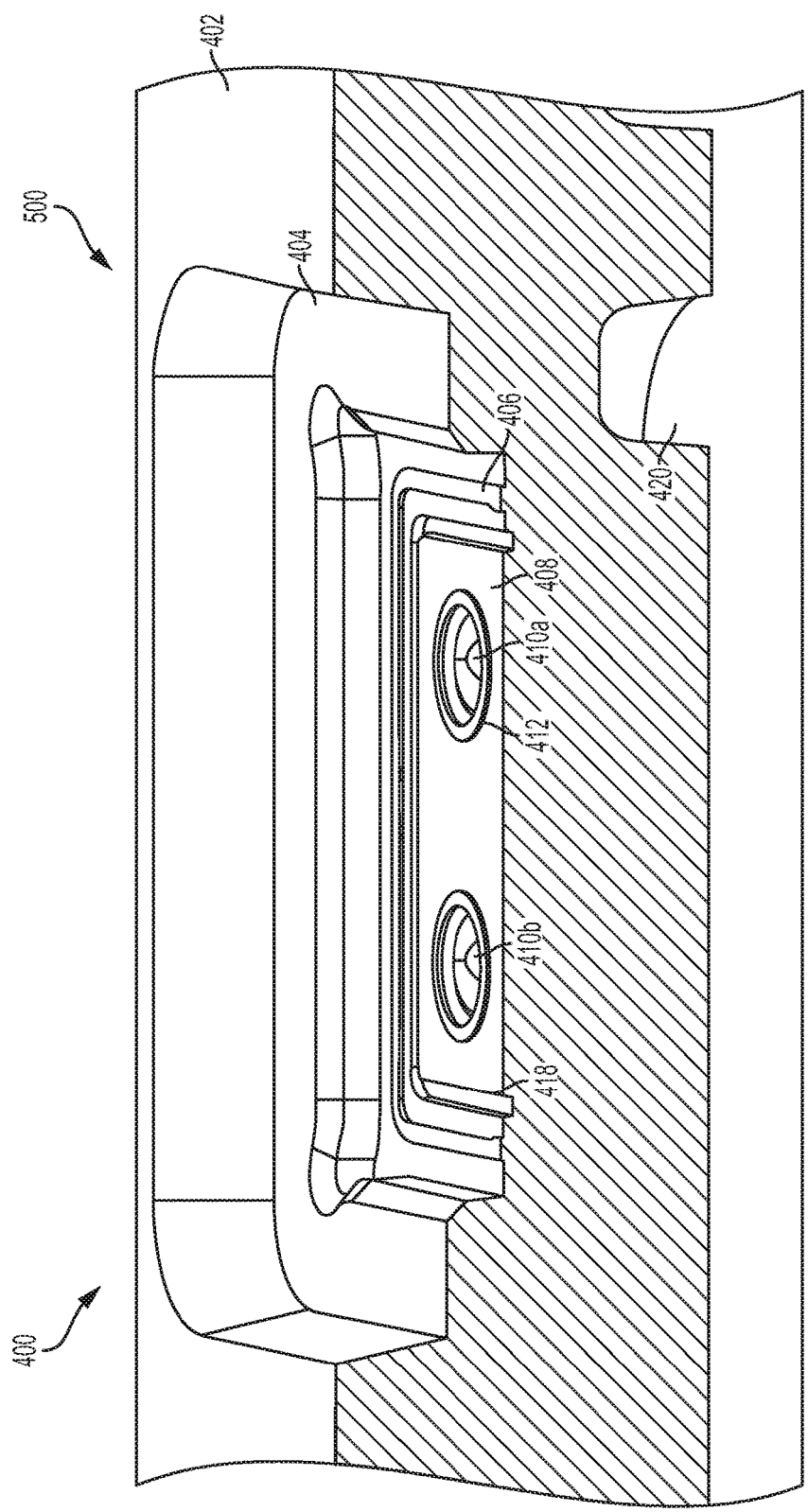
FIG. 5 is a schematic diagram of a sectional view of a portion of a microfluidic chip in accordance with embodiments of the present disclosure.

FIG. 5 is a schematic diagram of a sectional view A-A 500 of a portion of a microfluidic chip in accordance with embodiments of the present disclosure. The microfluidic chip 400 includes a top surface 402. The first intermediate surface 404 is shown as a step down from the top surface 402. In embodiments, the first intermediate surface 404 creates a glue stop and glue application point for a sensor die 250 to be clamped onto the microfluidic chip. The second intermediate surface 408 is shown as a step down from the first intermediate surface 404. The second intermediate surface 404 includes a glue stop 406 that surrounds a set of openings (e.g., opening 410a and 410b) to a microfluidic channel 420. The second intermediate surface 404 also includes a clamping bump 412 that surrounds each opening 410. In embodiments, the second intermediate surface 408 can include a trench 418 that can act as an additional glue stop. The trench 418 can be between the glue stop 406 and the set of openings.

Figure 6A:
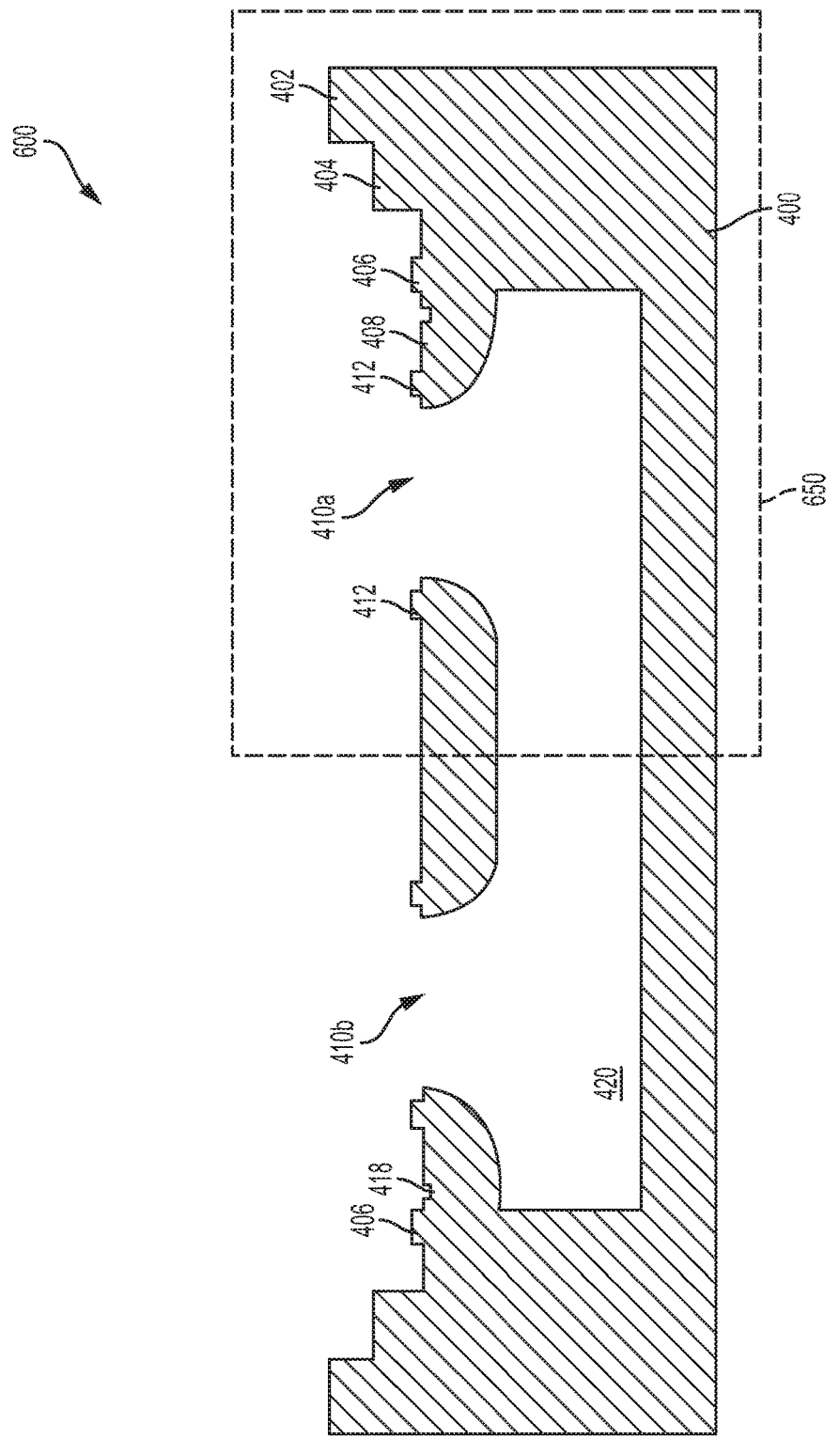
FIG. 6A is a schematic diagram of a side sectional view of a microfluidic chip in accordance with embodiments of the present disclosure.

FIG. 6A is a schematic diagram of a side sectional view B-B 600 of a microfluidic chip 400 in accordance with embodiments of the present disclosure. The side sectional view 600 illustrates the opening 410 that exposes the microfluidic channel 420. The side sectional view 600 illustrates the top surface 402, the first intermediate surface 404 stepped down from the top surface 402; and second intermediate surface 408 stepped down from the first intermediate surface 404. The glue stop 406 is shown extending from the second intermediate surface 408 and surrounding the openings 410a and 410b. The second intermediate surface 408 also includes a clamping bump 412 surrounding each opening (e.g., opening 410a). A trench 418 can be between the clamping bump 412 and the glue stop 406. The trench 418 can act as an additional glue stop for clamping the sensor die 250 onto microfluidic chip 400.

Figure 6B:
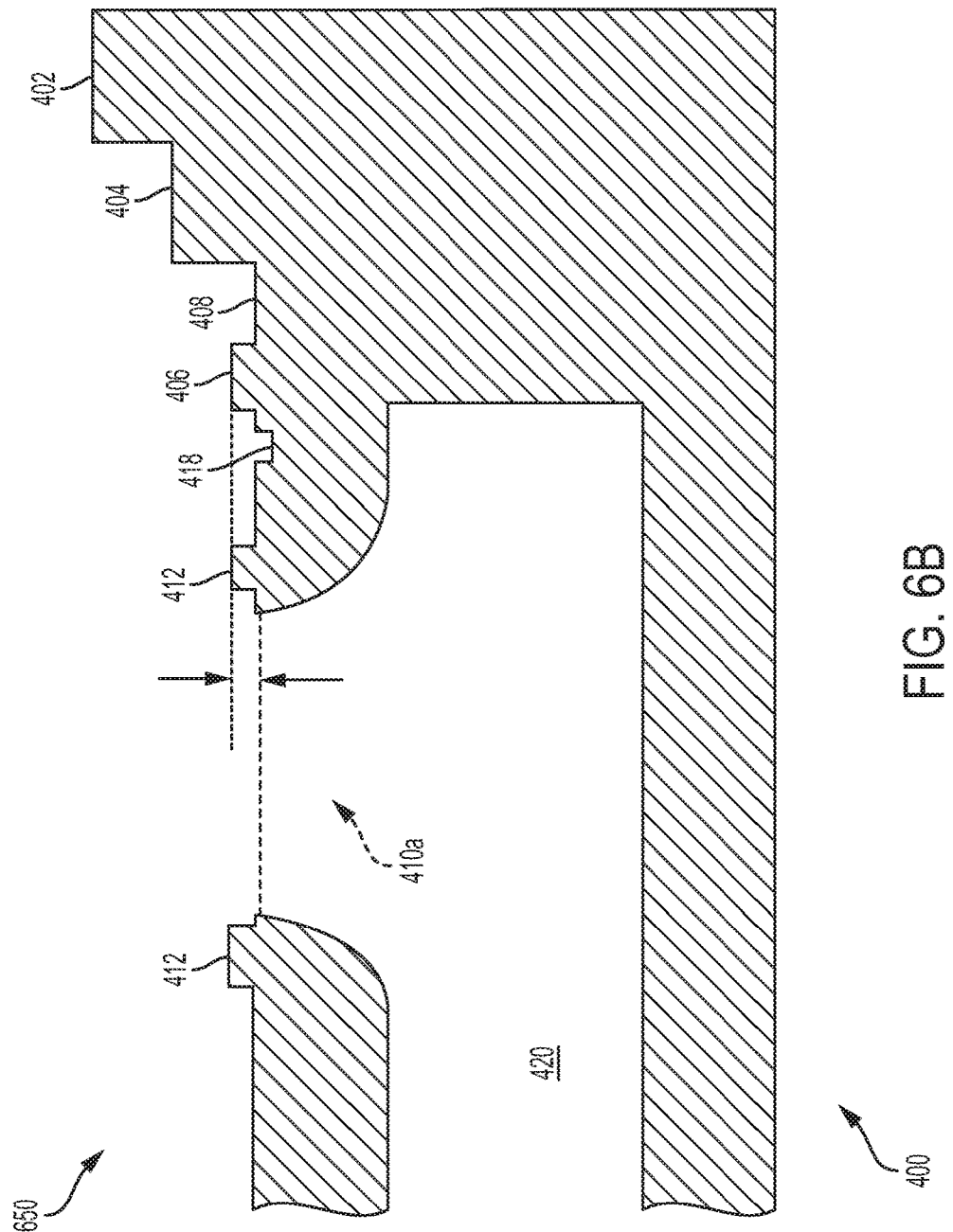
FIG. 6B is a schematic diagram of a close-up view of the microfluidic chip of FIG. 6A in accordance with embodiments of the present disclosure.

FIG. 6B is a schematic diagram of a close-up view of the microfluidic chip of FIG. 6A in accordance with embodiments of the present disclosure. As shown in FIG. 6B, the clamping bump 412 can be the same or similar height as the glue stop 406.

Figure 6C:
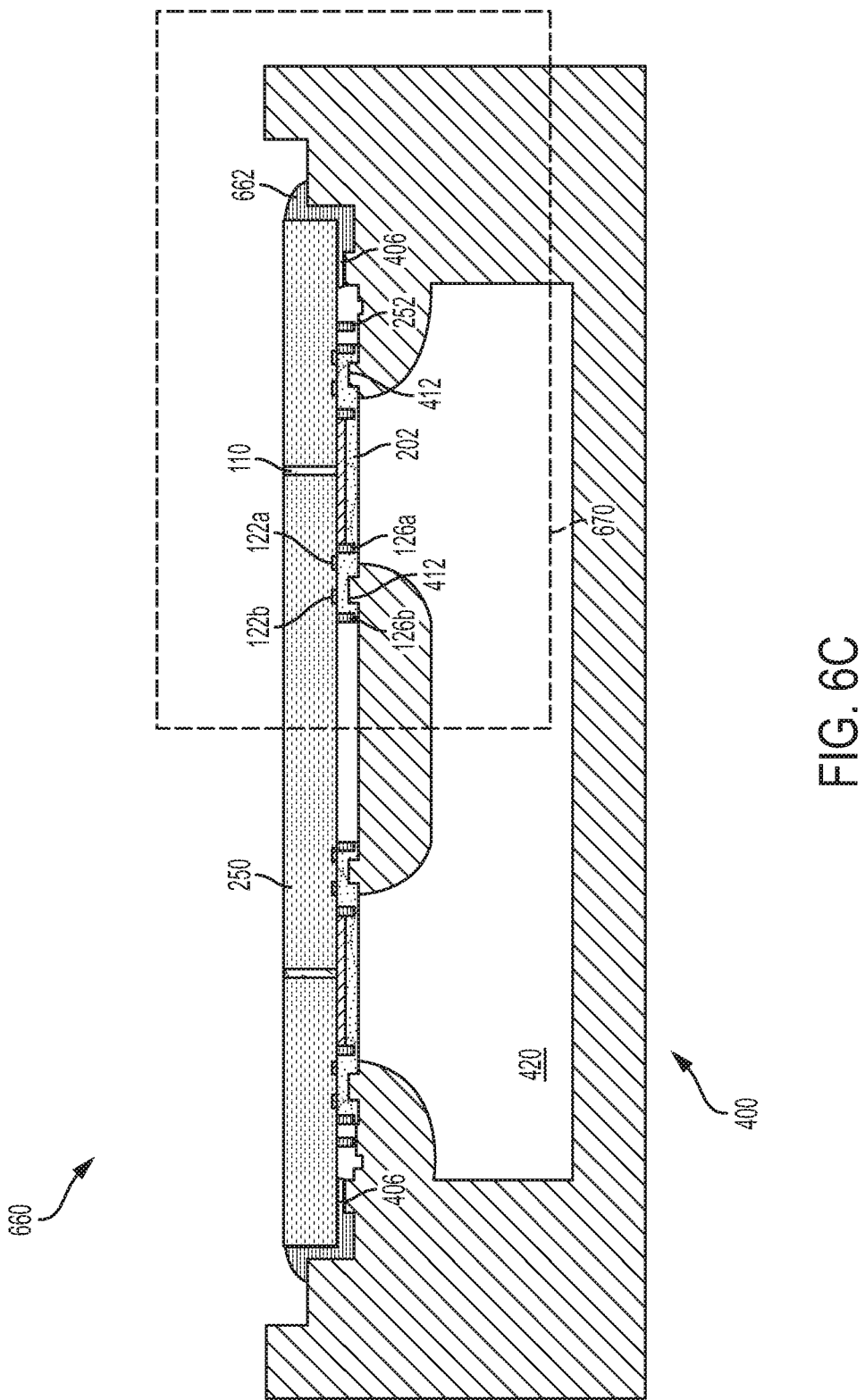
FIG. 6C is a schematic diagram of a side sectional view of a sensor die clamped to a microfluidic chip in accordance with embodiments of the present disclosure.

FIG. 6C is a schematic diagram of a side sectional view 660 of a sensor die 250 clamped to a microfluidic chip 400 in accordance with embodiments of the present disclosure. The sensor die 250 is placed onto the microfluidic chip 400 under an applied pressure. While under pressure, an adhesive 662 is applied to a gap between the first intermediate surface 404 and the second intermediate surface 408. The adhesive 662 is cured under pressure. An example adhesive is a UV-cured acrylated urethane, though other adhesives can be used. The sensors are aligned over the openings 410a and 410b. The clamping bump 412 contacts the membrane 202 in a location between rings 126a and 126b. The applied pressure can cause the membrane 202 to be compressed into the gripping trenches 122a and 122b.

Figure 6D:
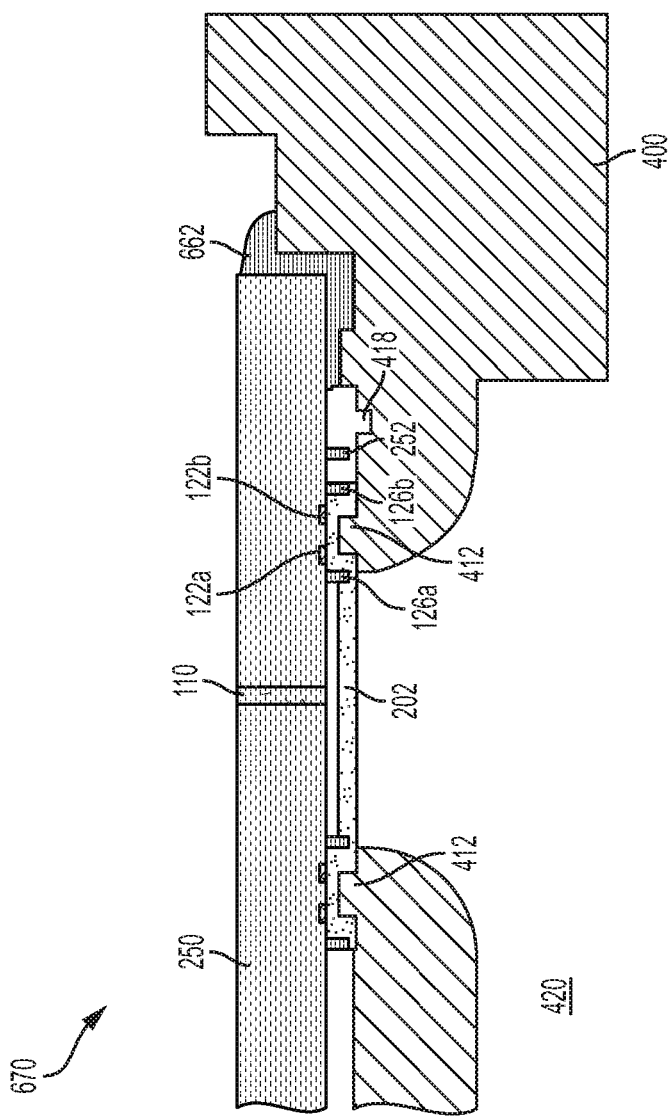
FIG. 6D is a schematic diagram of a close-up view of a sensor die clamped to the microfluidic chip of FIG. 6C in accordance with embodiments of the present disclosure.

FIG. 6D is a schematic diagram of a close-up view 670 of a sensor die 250 clamped to the microfluidic chip 400 of FIG. 6C in accordance with embodiments of the present disclosure. The close-up view 670 illustrates the clamping bump 412 in contact with the membrane 202 at a location between the rings 126a and 126b. The applied pressure of the sensor die 250 onto the clamp 412 pushes on the membrane 202 such that the membrane compresses into the trenches 122a and 122b. The close-up view 670 also illustrates the glue-stop trench 418.

Figure 7A:
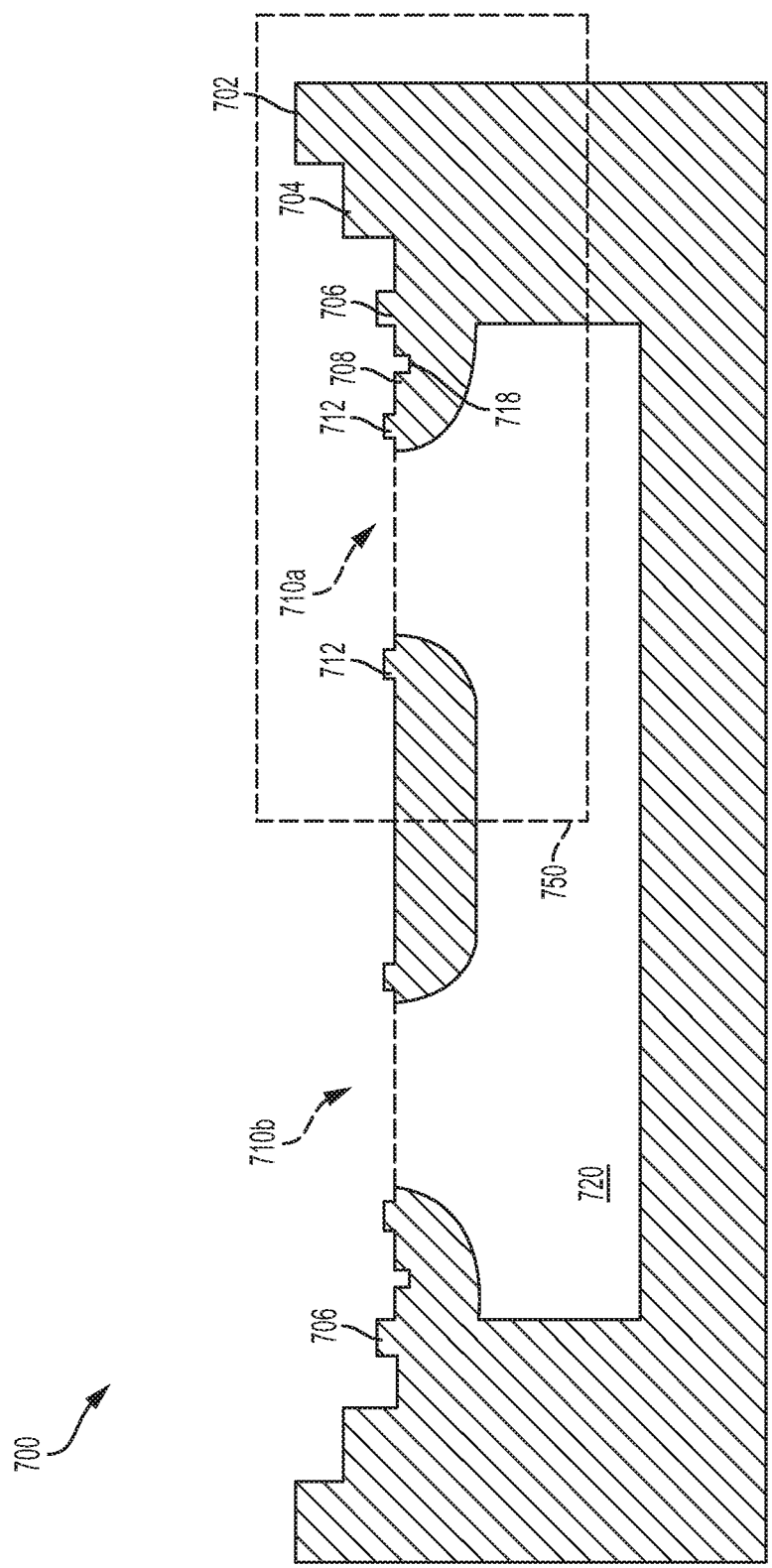
FIG. 7A is a schematic diagram of a side sectional view of a microfluidic chip in accordance with embodiments of the present disclosure.

FIG. 7A is a schematic diagram of a side sectional view of a microfluidic chip 700 in accordance with embodiments of the present disclosure. The side sectional view 700 illustrates the opening 710 that exposes the microfluidic channel 720. The side sectional view 700 illustrates the top surface 702, the first intermediate surface 704 stepped down from the top surface 702; and second intermediate surface 708 stepped down from the first intermediate surface 704. The glue stop 706 is shown extending from the second intermediate surface 708 and surrounding the openings 710*a* and 710*b*. The second intermediate surface 708 also includes a clamping bump 712 surrounding each opening (e.g., opening 710*a*). A trench 718 (shown in FIG. 7B) can be between the clamping bump 712 and the glue stop 706. The trench 718 can act as an additional glue stop for clamping the sensor die 250 onto microfluidic chip 700.

Figure 7B:
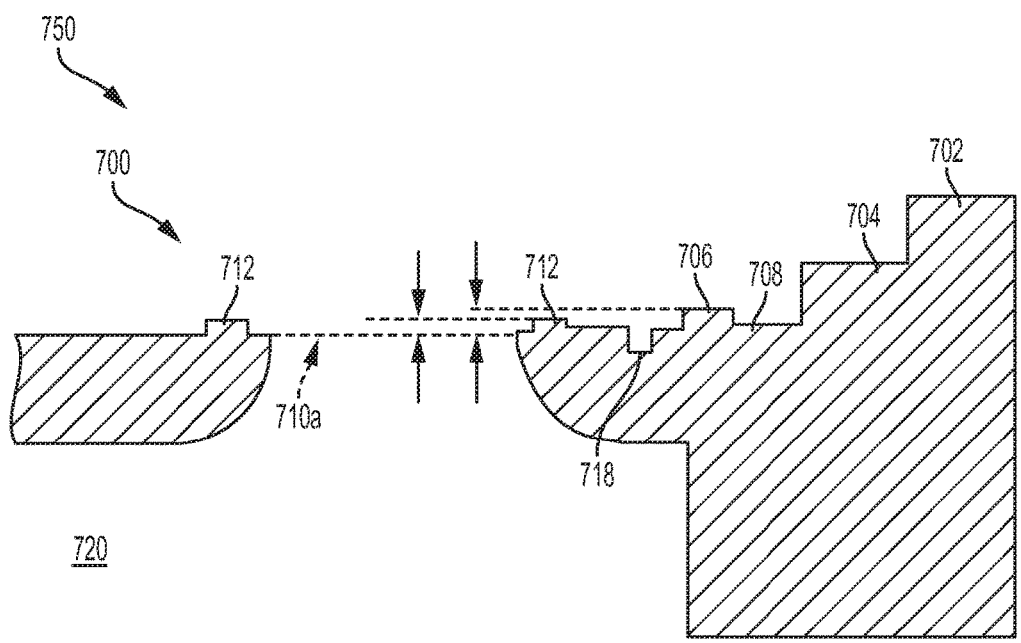
FIG. 7B is a schematic diagram of a close-up view of the microfluidic chip of FIG. 7A in accordance with embodiments of the present disclosure.

FIG. 7B is a schematic diagram of a close-up view 750 of the microfluidic chip of FIG. 7A in accordance with embodiments of the present disclosure. As shown in FIG. 7B, the clamping bump 712 can be at a lower height than the glue stop 706.

Figure 7C:
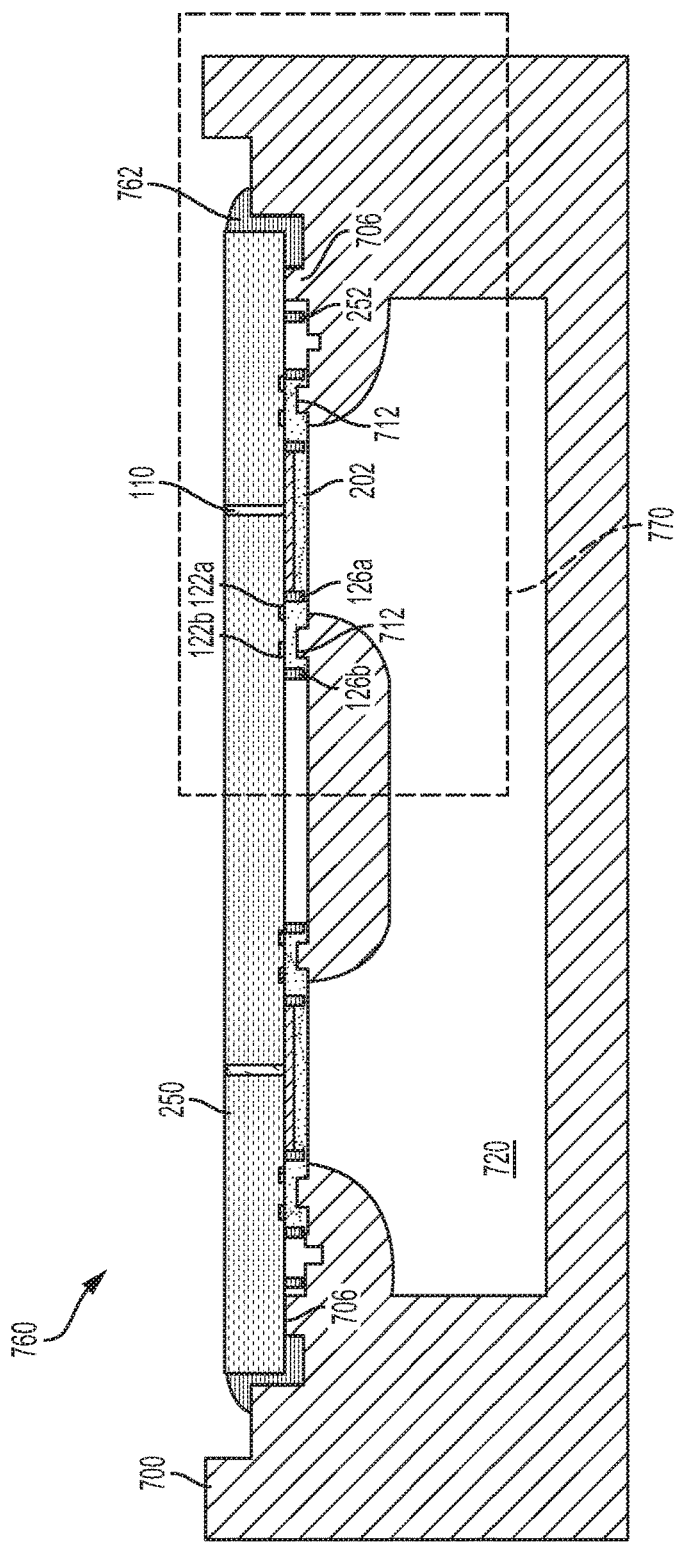
FIG. 7C is a schematic diagram of a side sectional view of a sensor die clamped to a microfluidic chip in accordance with embodiments of the present disclosure.

FIG. 7C is a schematic diagram of a side sectional view 760 of a sensor die 250 clamped to a microfluidic chip 700 in accordance with embodiments of the present disclosure. The sensor die 250 is placed onto the microfluidic chip 700 under an applied pressure. While under pressure, an adhesive 762 is applied to a gap between the first intermediate surface 704 and the second intermediate surface 708. The adhesive 762 is cured under pressure. The sensors are aligned over the openings 710*a* and 710*b*. The clamping bump 712 contacts the membrane 202 in a location between rings 126*a* and 126*b*. The applied pressure can cause the membrane 202 to compress into the gripping trenches 122*a* and 122*b*. The glue stop 706 can contact the sensor die 250 due to the glue stop 706 height being taller than the clamping bump 712. The contact made between the glue stop 706 and the sensor die 250 can further aide in preventing the adhesive 762 from contacting the membrane 202 or other parts of the sensor. Glue stop 706 can act as a spacer or hard stop for the sensor die 250.

Figure 7D:
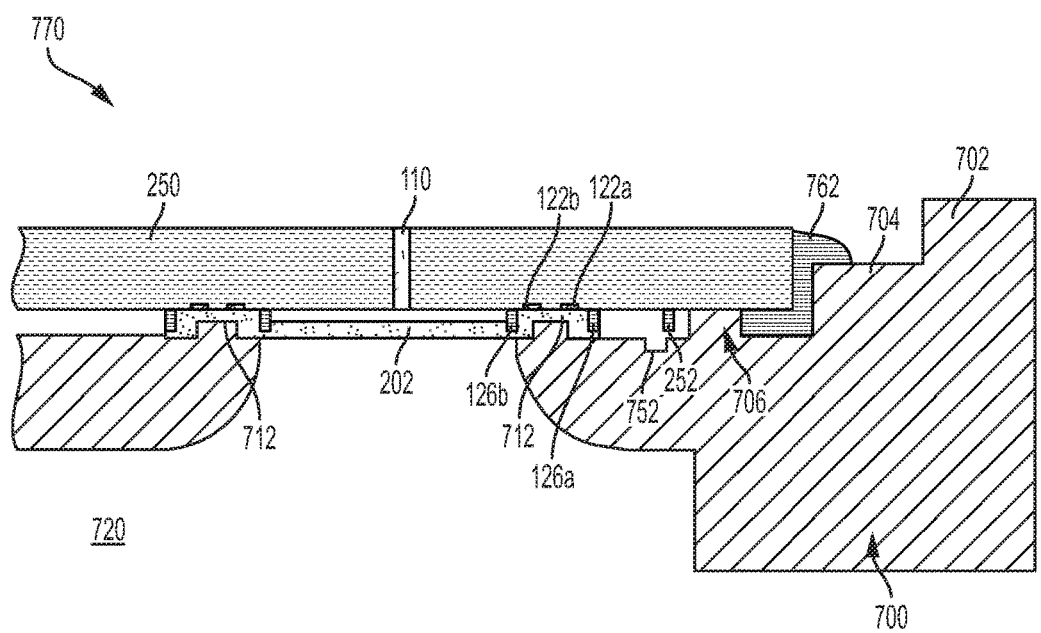
FIG. 7D is a schematic diagram of a close-up view of a sensor die clamped to the microfluidic chip of FIG. 7C in accordance with embodiments of the present disclosure.

FIG. 7D is a schematic diagram of a close-up view 770 of a sensor die 250 clamped to the microfluidic chip 700 of FIG. 7C in accordance with embodiments of the present disclosure. The close-up view 770 illustrates the clamping bump 712 in contact with the membrane 202 at a location between the rings 126*a* and 126*b*. The applied pressure of the sensor die 250 onto the clamp 712 pushes on the membrane 202 such that the membrane compresses into the trenches 122*a* and 122*b*. The close-up view 770 also illustrates the glue-stop trench 718.

Figure 8A:
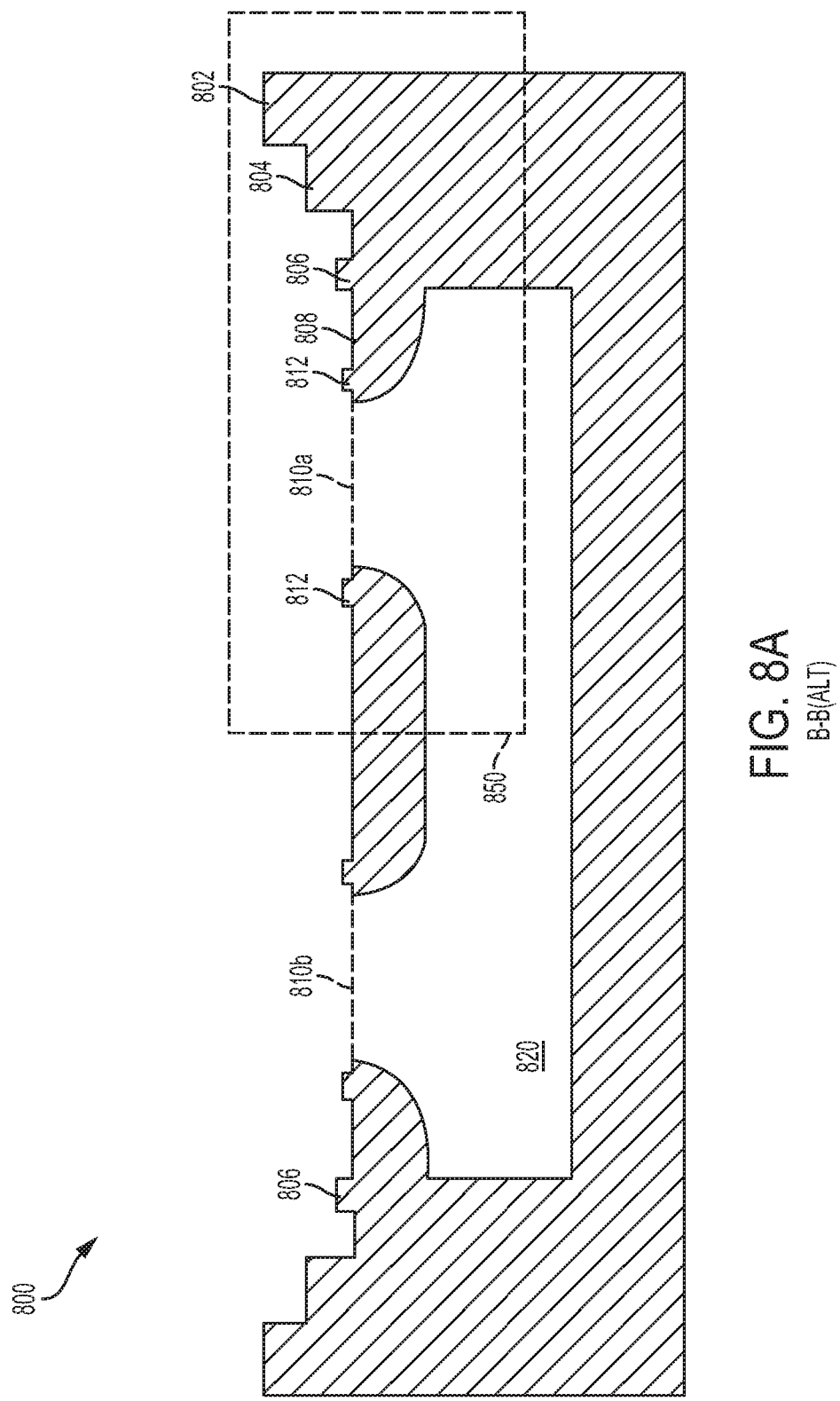
FIG. 8A is a schematic diagram of a side sectional view of a microfluidic chip in accordance with embodiments of the present disclosure.

FIG. 8A is a schematic diagram of a side sectional view of a microfluidic chip 800 in accordance with embodiments of the present disclosure. The microfluidic chip 800 includes an opening 810 that exposes the microfluidic channel 820. The side sectional view 800 illustrates the top surface 802, the first intermediate surface 804 stepped down from the top surface 802; and second intermediate surface 808 stepped down from the first intermediate surface 804. The glue stop 806 is shown extending from the second intermediate surface 808 and surrounding the openings 810*a* and 810*b*. The second intermediate surface 808 also includes a clamping bump 812 surrounding each opening (e.g., opening 810*a*). The microfluidic chip 800 does not include a trench between the glue stop 806 and the clamping bump 812.

Figure 8B:
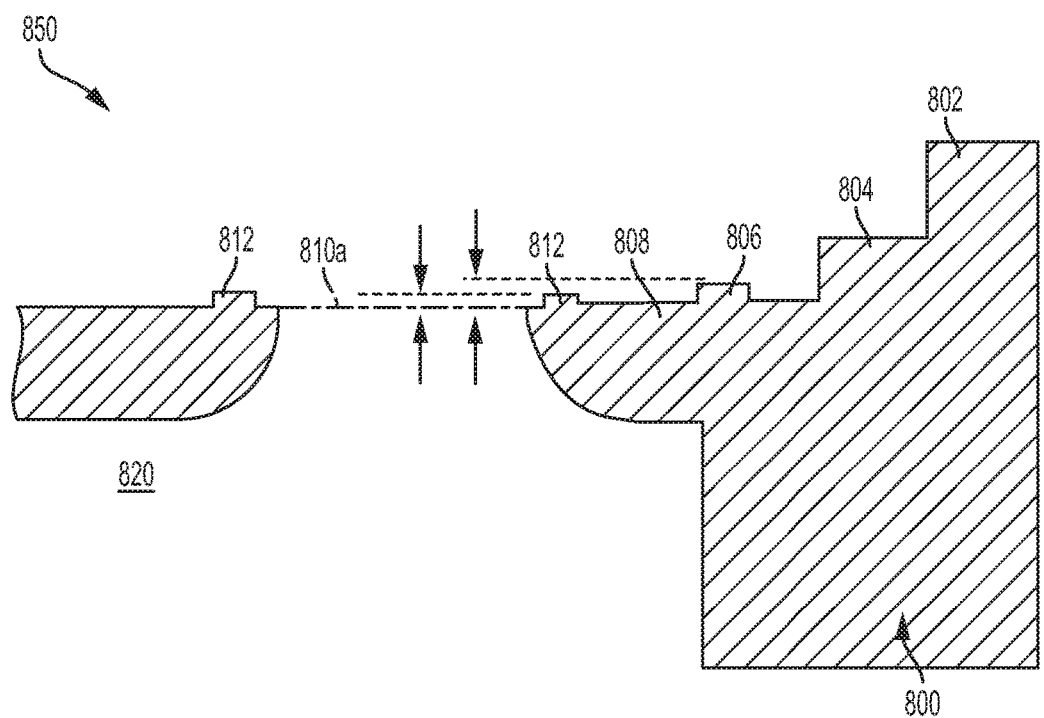
FIG. 8B is a schematic diagram of a close-up view of the microfluidic chip of FIG. 8A in accordance with embodiments of the present disclosure.

FIG. 8B is a schematic diagram of a close-up view 850 of the microfluidic chip of FIG. 8A in accordance with embodiments of the present disclosure. As shown in FIG. 8B, the clamping bump 812 can be at a lower height than the glue stop 806.

Figure 9B:
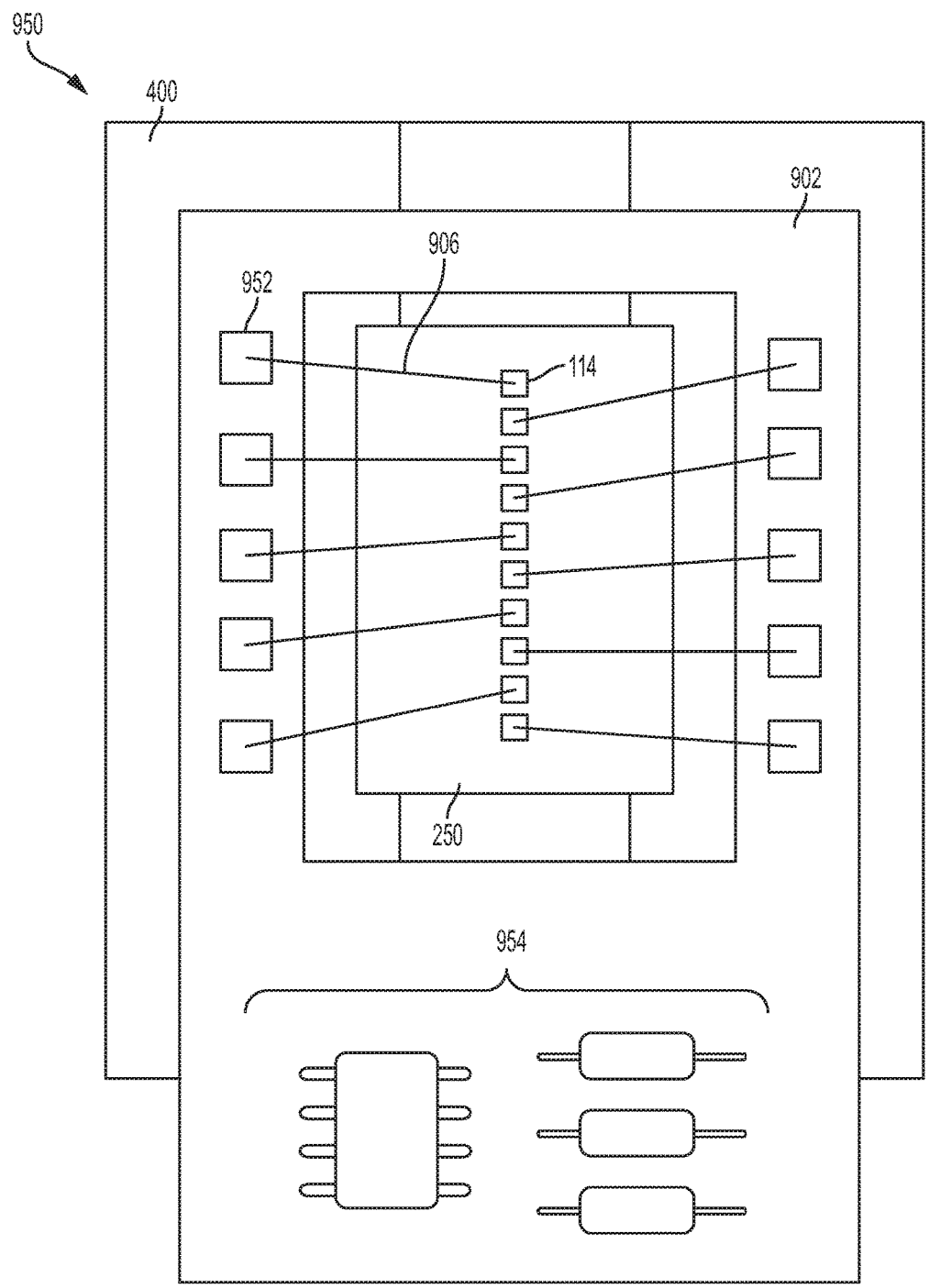
FIG. 9B is a schematic diagram of a top-down view of the sensor die clamped to a microfluidic chip and electrically coupled to a printed circuit board of FIG. 9A in accordance with embodiments of the present disclosure.

FIG. 9A is a schematic diagram of a side sectional view 900 of a sensor die 250 clamped to a microfluidic chip 400 and electrically coupled to a printed circuit board 902 in accordance with embodiments of the present disclosure. Microfluidics chip 400 is similar to microfluidics chip 400 shown in FIGS. 4-6D, but can also be similar to microfluidic chip 700 of FIGS. 7A-7D or microfluidic chip 800 of FIGS. 8A-B. The sensor die 250 is clamped to the microfluidic chip 400 by an adhesive (such as adhesive substance 662 or adhesive substance 762) that is applied while the sensor die 250 is pushed down onto the microfluidic chip 400 and cured. A printed circuit board 902 can be adhered to the top surface 402 of the microfluidic chip 400 by an adhesive 904. Adhesive 904 can be an adhesive tape, double sided tape, glue, or other known technique of affixing a rigid structure onto the microfluidic chip 400. The printed circuit board 902 can include one or more contact pads 952 (shown in FIG. 9B) that are electrically connected to other circuit elements 954 (some of which are represented in FIG. 9B) through conductive traces (not shown). Each sensor 100 can be electrically connected to the printed circuit board 902 via wire bonds 906. After wire bonding has been completed, an encapsulant 908 can be applied over at least a portion of the printed circuit board 902 to protect the wire bond 906 and to electrically insulate the contact pads. The encapsulant can be a UV-cured modified urethane.

FIG. 9B is a schematic diagram of a top-down view 950 of the sensor die clamped to a microfluidic chip and electrically coupled to a printed circuit board of FIG. 9A in accordance with embodiments of the present disclosure. FIG. 9B illustrates the sensor die 250 that includes sensor contacts 114. Sensor contacts 114 are electrically connected to the ISE of the sensor through a via 110 (shown in FIG. 9A). The sensor contacts 114 are electrically connected to contact pads 952 on PCB 902 via wire bonds 906. As shown, the PCB 902 can also include electrical components 954 that can perform various functions including applying bias to the sensor, detecting electrical signals from the sensor, and other functions.

Figure 10A:
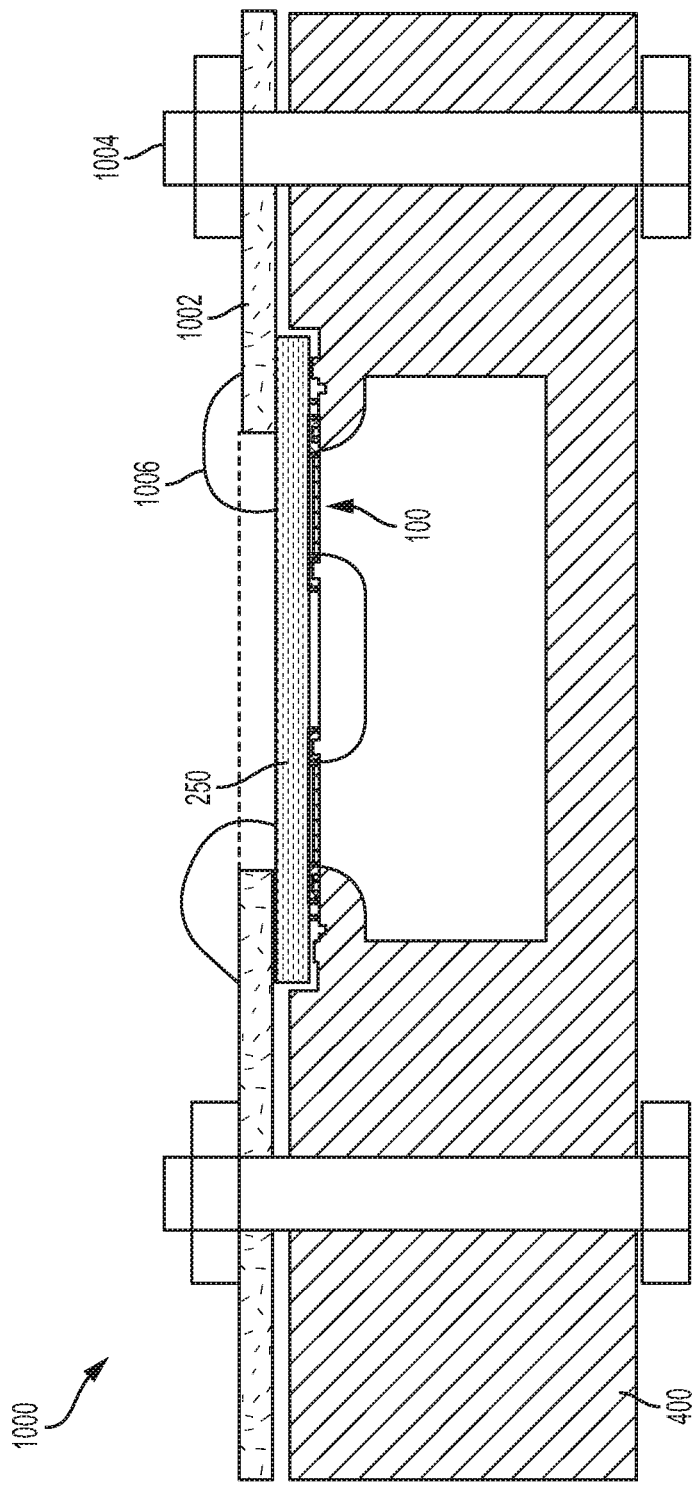
FIG. 10A is a schematic diagram of a side sectional view of a sensor die clamped to a microfluidic chip and secured to the microfluidic chip by screws in accordance with embodiments of the present disclosure.

FIG. 10A is a schematic diagram of a side sectional view 1000 of a sensor die 250 clamped to a microfluidic chip 400 and secured to the microfluidic chip by screws 1004 in accordance with embodiments of the present disclosure. A rigid structure 1002 can be used to provide electrical connectivity between the sensor 100 and outside electronics, as well as to provide structural stability for securing the sensor die 250 to the microfluidic chip 400. The rigid structure 1002 can be a PCB, a metal surface, a polymer surface, etc. The microfluidic chip 400 and the rigid structure 1002 can include through holes for receiving screws 1004, which are secured using a locking nut in this embodiment.

Figure 10B:
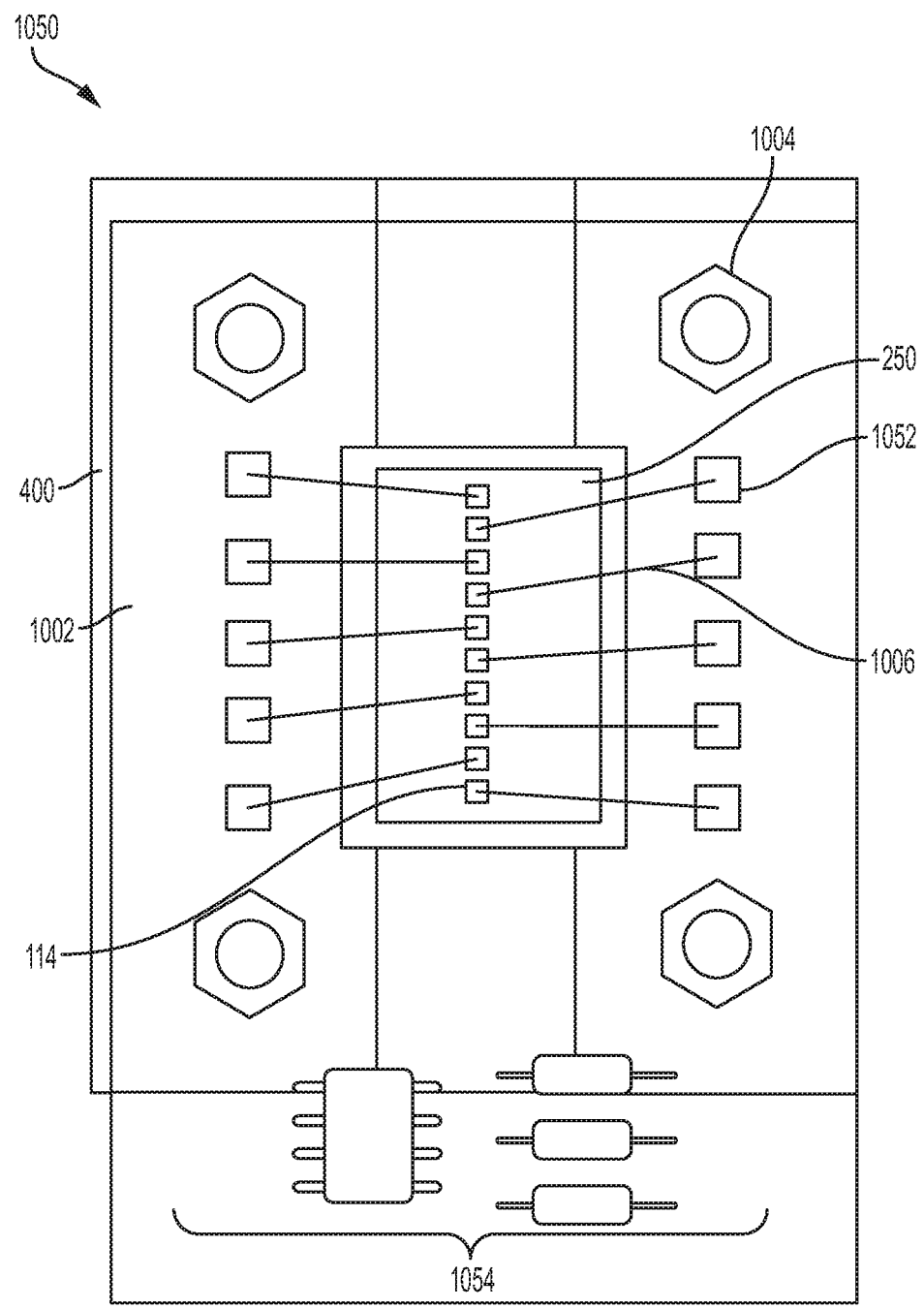
FIG. 10B is a schematic diagram of a top-down view of a sensor die clamped to a microfluidic chip of FIG. 10A in accordance with embodiments of the present disclosure.

FIG. 10B is a schematic diagram of a top-down view 1050 of a sensor die 250 clamped to a microfluidic chip 400 of FIG. 10A in accordance with embodiments of the present disclosure. FIG. 10A illustrates the rigid structure 1002 to include contact pads 1052 that can electrically connect contacts 114 on the sensor to outside electronics (e.g., electronics 1054) via a wire bond 1006. The screw 1004 are shown to secure the rigid structure 1002 to the microfluidic chip 400 with nuts.

Aspects described in this disclosure can employ thin-film fabrication techniques to create the sensor devices and structures described herein, and to achieve advantages that are described herein and that are readily apparent to those of skill in the art.

Advantages of the present disclosure are readily apparent. Advantages of using the through-silicon via to connect to the micro ion-selective electrode may include the following:

While certain embodiments have been described in detail, those familiar with the art to which this disclosure relates will recognize various additional and/or alternative designs, embodiments, and process steps for making and using the sensor device as described by the following claims.

What is claimed is:

1. A microfluidic chip comprising a top surface and an intermediate surface, the intermediate surface defining a microfluidic channel comprising:
   a microfluidics channel in the microfluidic chip;
   an opening in the intermediate surface exposing the microfluidic channel;
   a first surface surrounding the opening; and
   a solid-state chemical sensor residing on a sensor die, at least a portion of the solid-state chemical sensor in contact with the first surface of the microfluidic chip, the solid-state chemical sensor exposed to the microfluidics channel.

2. The microfluidic chip of claim 1, wherein the solid-state chemical sensor comprises:
   a sensor substrate residing on the microfluidic chip, the sensor substrate comprising a sensor device residing on a sensor-side of the substrate, the sensor-side of the sensor device facing the microfluidics channel, the sensor device comprising:
      a sensor-side electrode on the sensor-side of the substrate, the sensor-side electrode facing the microfluidics channel;
      a first polymer ring surrounding the sensor-side electrode;
      a second polymer ring surrounding the first polymer ring;
      a polymeric membrane encapsulating the sensor-side electrode and being contained by the second polymer ring.

3. The microfluidic chip of claim 2, wherein the first surface is in contact with the polymeric membrane at a location between the first polymer ring and the second polymer ring, the first surface clamping the sensor die to the microfluidic chip.

4. The microfluidic chip of claim 2, further comprising a second raised surface surrounding the first surface; and
   wherein the substrate of the sensor device contacts the second raised surface.

5. The microfluidic chip of claim 4, wherein the second raised surface defines an open space between the top surface and the intermediate surface, the microfluidic chip further comprising an adhesive substance in the space, the adhesive substance contacting the substrate, and securing the substrate to the intermediate surface.

6. The microfluidic chip of claim 1, wherein the sensor die comprises a plurality solid-state chemical sensors, each of the plurality of solid-state chemical sensors exposed to the microfluidics channel.

7. The microfluidic chip of claim 1, wherein the first surface is a first raised surface, the microfluidic chip further comprises a second raised surface adjacent the first raised surface.

8. The microfluidic chip of claim 7, wherein the first raised surface is lower in height than the second raised surface.

9. The microfluidic chip of claim 8, wherein the second raised surface contacts the sensor die.

10. The microfluidic chip of claim 7, further comprising a trench between the first raised surface and the second raised surface.

11. The microfluidic chip of claim 1, wherein the sensor die is clamped to the microfluidic chip by an adhesive.

12. The microfluidic chip of claim 1, wherein the sensor die comprises a sensor side and a backside, the backside comprising:
   a backside electrode; and
   the sensor die comprising a through-silicon via electrically connecting the sensor-side and the backside electrode.

13. The microfluidic chip of claim 12, further comprising a rigid structure affixed to the microfluidic chip.

14. The microfluidic chip of claim 13, wherein the rigid structure comprises a printed circuit board, the printed circuit board comprising a contact pad, the backside electrode electrically connected to the contact pad by a wire.

15. The microfluidic chip of claim 13, wherein the rigid structure is affixed to the microfluidic chip by one or more screws.

16. The microfluidic chip of claim 13, wherein the rigid structure is affixed to the microfluidic chip by double sided tape.

17. The microfluidic chip of claim 1, wherein the sensor die comprises a plurality of sensor devices.

18. The microfluidic chip of claim 1, wherein the opening is defined by a conical shape exposing the microfluidics channel.

19. A method for forming a microfluidic system comprising a sensor device, the method comprising:
   providing a microfluidic chip, the microfluidic chip comprising a sensor device mounting surface, the sensor device mounting surface comprising an opening revealing a microfluidic channel and a first raised surface surrounding the opening and a second raised surface surrounding the first raised surface;
   providing a substrate with a chemical sensor device onto the sensor device mounting surface, the chemical sensor device comprising an ion-selective sensor facing the microfluidic channel, the chemical sensor device further comprising a polymeric membrane facing the microfluidic channel, the substrate contacting the second raised surface and the first raised surface contacting the membrane between two polymeric rings;
   applying a compressive load to the substrate in a direction towards the sensor device mounting surface;
   applying an adhesive substance to the substrate and an outer sidewall of the second raised surface; and
   curing the adhesive substance under the compressive load.

20. The method of claim 19, wherein the chemical sensor comprises an electrode on a backside of the chemical sensor device electrically connected to the ion selective sensor and opposite the microfluidic channel, the method further comprising:
   adhering a printed circuit board to the microfluidic chip, the printed circuit board comprising an electrical contact pad; and
   electrically connecting the electrode on the backside of the chemical sensor to the electrical contact pad on the printed circuit board.

* * * * *